US006218396B1

(12) United States Patent
Kuo et al.

(10) Patent No.: US 6,218,396 B1
(45) Date of Patent: Apr. 17, 2001

(54) SUBSTITUTED PYRIDINO ARYLPIPERAZINES USEFUL IN THE TREATMENT OF BENIGN PROSTATIC HYPERPLASIA

(75) Inventors: Gee-Hong Kuo, Scotch Plains; William V. Murray, Belle Mead, both of NJ (US); Catherine P. Prouty, Doylestown, PA (US)

(73) Assignee: Orth-McNeil Pharmaceutical, Inc., Raritan, NJ (US)

( * ) Notice: Subject to any disclaimer, the term of this patent is extended or adjusted under 35 U.S.C. 154(b) by 45 days.

(21) Appl. No.: 09/252,313

(22) Filed: Feb. 18, 1999

Related U.S. Application Data
(60) Provisional application No. 60/075,321, filed on Feb. 20, 1998.

(51) Int. Cl.[7] ........................ A61K 31/496; C07D 401/12
(52) U.S. Cl. ........................ 514/253.01; 544/365
(58) Field of Search ............................ 544/365; 514/252, 514/253.01

(56) References Cited

U.S. PATENT DOCUMENTS 5,403,847   4/1995   Gluchowski et al. ............... 514/318

FOREIGN PATENT DOCUMENTS

| 4425146 | * | 1/1996 | (DE) . |
| 496692 | * | 7/1992 | (EP) . |
| 0 711 757 | | 5/1996 | (EP) . |
| 99/03833 | * | 1/1999 | (WO) . |

OTHER PUBLICATIONS

Breslin D, Fields DW, Chou T–C, Marion DN, Kane M, Vaughan ED, and Felsen D (1993) Medical management of benign prostatic hyperplasia: a canine model comparing the in vivo efficacy of alpha–1 adrenergic antagonists in the prostate. J. Urol. 149: 395–399.

Bruno JF, Whittaker J, Song J, and Berelowitz M. (1991) Molecular cloning and sequencing of a cDNA encoding a human α1A adrenergic receptor. Biochem. Biophys. Res. Commun. 179: 1485–1490.

Bylund DB, Eikenberg DC, Hieble JP, Langer SZ, Lefkowitz RJ, Minneman KP, Molinoff PB, Ruffolo RR, and Trendelenburg U (1994) IV. International Union of Pharmacology nomenclature of adrenoceptors. Pharmacol. Rev. 46: 121–136.

Carruthers SG (1994) Adverse effects of α1–adrenergic blocking drugs. Drug Safety 11: 12–20.

Faure C, Gouhier C, Langer SZ, and Graham D (1995) Quantification of α1–adrenoceptor subtypes in human tissues by competetive RT–PCR analysis. Biochem. Biophys. Res. Commun. 213: 935–943.

Flavahan NA and VanHoutte PM (1986) α1–Adrenoceptor subclassification in vascular smooth muscle. Trends Pharmacol. Sci. 7: 347–349.

Ford APDW, Arredondo NF, Blue DR, Bonhaus DW, Jasper J Kava MS, Lesnick J, Pfister JR, Shieh IA, Vimont RL, Williams TJ, McNeal JE, Stamey TA, and Clarke DE (1996) RS–17053 (N–[2–(2–Cyclopropylmethoxyphenoxy)ethyl] –5–chloro-a, a–dimethyl–1H–indole–3–ethanamine hydrochloride), a selective α1A–adrenoceptor antagonist, displays low affinity for functional α1–adrenoceptors in human prostate: Implications for adrenoceptor classification. Mol. Pharmacol. 49: 209–215.

Forray C, Bard JA, Wetzel JM, Chiu G, Shapiro E, Tang R, Lepor H, Hartig PR, Weinshank RL, Branchek TA, and Gluchowski C (1994) The α1–adrenergic receptor that mediates smooth muscle contraction in human prostate has the pharmacological properties of the cloned human α1c subtype. Mol. Pharmacol. 45: 703–708.

Gormley G, Stoner E, Bruskewitz RC et al. (1992) The effect of finasteride in men with benign prostatic hyperplasia. N. Engl. J. Med. 327: 1185–1191.

Hatano A, Takahashi H, Tamaki M, Komeyama T, Koizumi T, and Takeda M (1994) Pharmacological evidence of distinct α1–adrenoceptor subtypes mediating the contraction of human prostatic urethra and peripheral artery. Br. J. Pharmacol. 113: 723–728.

Harrison JK, Pearson WR, and Lynch KR (1991) Molecular characterization of α1– and α2–adrenoceptors. Trends Pharmacol. Sci. 12: 62–67.

(List continued on next page.)

Primary Examiner—Emily Bernhardt
(74) Attorney, Agent, or Firm—Ruby T. Hope

(57) ABSTRACT

This invention relates a to a series of heterocyclic substituted piperazines of Formula I

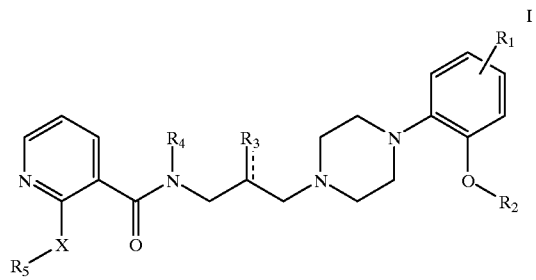

methods of treatment, pharmaceutical compositions containing them, and intermediates used in their manufacture. The compounds of the invention selectively inhibit binding to the α-1$_a$ adrenergic receptor, a receptor which has been implicated in benign prostatic hyperplasia. As such the compounds are potentially useful in the treatment of this disease.

12 Claims, 1 Drawing Sheet

OTHER PUBLICATIONS

Figure 1:
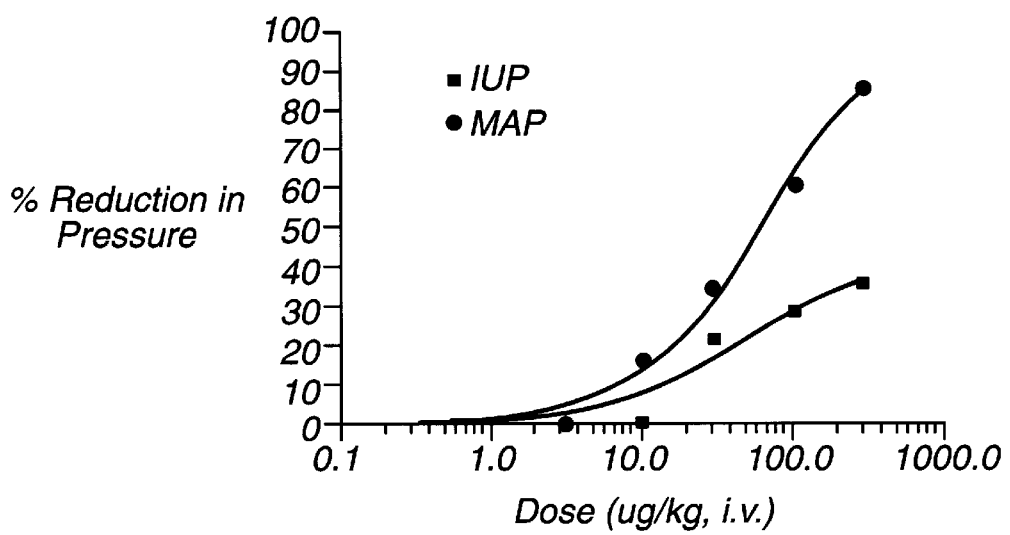

Hieble JP and Caine M (1986) Etiology of benign prostatic hyperplasia and approaches to pharmacological management. Fed. Proc. 45: 2601–2603.

Hirasawa A, Horie K, Tanaka T, Takagaki K, Murai M, Yano J, and Tsujimoto G (1993) Cloning, functional expression and tissue distribution of human cDNA for the α1c–adrenergic receptor. Biochem. Biophys. Res. Commun. 195: 902–909.

Holck MI, Jones CHM, and Haeusler G (1983) Differential interactions of clonidine and methoxamine with postsynaptic α–adrenoceptor of rabbit main pulmonary artery. J.Cardiovasc. Pharm. 5: 240–248.

Lepor H and Rigaud G (1990) The efficacy of transurethral resection of the prostate in men with moderate symptoms of prostatism J. Urol. 143:533–537.

Lepor H, Auerbach S, Puras–Baez A et al. (1992) A randomized placebo–controlled multicenter study of the efficacy and safety of terazosin in the treatment of benign prostatic hyperplasia. J. Urol. 148: 1467–1474.

Lepor H (1995) α–Blockade for benign prostatic hyperplasia (BPH) J. Clin. Endocrinol. Metab. 80: 750–753.

Marshall I, Burt RP, Andersson PO, Chapple CR, Greengrass PM, Johnson GI, and Wyllie MG (1992) Human α1c–adrenoceptor: functional characterisation in prostate. Br. J. Pharmacol. 107(Proc. Suppl. Dec.):327P.

Marshall I, Burt RP, and Chapple CR (1995) Noradrenaline contractions of human prostate mediated by α1A–(α1c–) adrenoceptor subtype. Br. J. Pharmacol. 115: 781–786.

Mebust WK, Holtgrewe HL, Cockett ATK, and Peters PC (1989) Transurethral prostatactomy: immediate and postoperative complications. A cooperative study of 13 participating institutions evaluating 3,885 patients.J. Urol.,141: 243–247.

Minneman KP, Han C and Abel PW (1988) Comparison of α1–adrenergic receptor subtypes distinguished by chloroethylclonidine and WB4101. Mol. Pharmacol. 33: 509–514.

Minneman KP and Esbenshade TA (1994) α1–Adrenergic receptor subtypes. Annu. Rev. Pharmacol. Toxicol. 34: 117–133.

Morrow AL and Creese I (1986) Characterization of α1–adrenergic receptor subtypes in rat brain: A reevaluation of [3H]WB4104 and [3H]prazosin binding. Mol. Pharmacol. 29: 321–330.

Muramatsu I (1992) A pharmacological perspective of α1–adrenoceptors: subclassification and functional aspects. (Fujiwara M, Sugimoto T, and Kogure K, eds.). Excerpta Medica Ltd., Tokyo, 193–202.

Muramatsu I, Oshita M, Ohmura T, Kigoshi S, Akino H, Gobara M, and Okada K (1994) Pharmacological characterization of α1–adrenoceptor subtypes in the human prostate: functional and binding studies. Br. J. Urol. 74: 572–577.

Oesterling JE (1995) Benign prostatic hyperplasia. Medical and minimally invasive treatment options. N. Engl. J. Med. 332: 99–109.

Price DT, Lefkowitz RJ, Caron MG, Berkowitz D, and Schwinn DA (1994) Localization of mRNA for three distinct α1–adrenergic receptor subtypes in human tissues: implications for human α–adrenergic physiology. Mol. Pharmacol. 45: 171–175.

Ramarao CS, Kincade Denker JM, Perez DM, Gaivin RJ, Riek RP, and Graham RM (1992) Genomic organization and expression of the human α1B–adrenergic receptor. J. Biol. Chem. 267: 21936–21945.

Schwinn DA, Johnston GI, Page SO, Mosley MJ, Wilson KH, Worman NP, Campbell S, Fidock MD, Furness LM, Parry–Smith DJ, Peter B, and Bailey DS (1995) Cloning and pharmacological characterization of human alpha–1 adrenergic receptors: sequence corrections and direct comparison with other species homologues. JPET 272: 134–142.

Steers W.D., Zorn B. (1995) Benign Prostatic Hyperplasia. Disease–a–Month. 7:441–497.

Weinberg DH, Trivedi P, Tan CP, Mitra S, Perkins–Barrow A, Borkowski D, Strader CD, and Bayne M (1994) Cloning, expression and characterization of human α adrenergic receptors α1A, α1B, and α1C. Biochem. Biophys. Res. Commun. 201: 1296–1304.

Weis KA, Epstein RS, Huse DM, Deverka PA and Oster G (1993) The costs of prostatectomy for benign prostatic hyperplasia. Prostate 22: 325–334.

Wennberg JE, Roos N, Sola L, Schori A, and Jaffe R (1987) Use of claims data systems to evaluate health care outcomes: mortality and reoperation following prestatectomy. JAMA 257: 933–936.

Yamada S, Tanaka C, Kimura R, and Kawabe K (1994) Alpha 1–adrenoceptors in human prostate: characterization and binding characteristics of alpha 1–antagonists. Life Sci. 54: 1845–1854.

* cited by examiner

Effects of Compound 8 upon IUP and MAP at 3 μg/kg PE in dogs

SUBSTITUTED PYRIDINO ARYLPIPERAZINES USEFUL IN THE TREATMENT OF BENIGN PROSTATIC HYPERPLASIA

This application is a continuation application under 1.53 (d) of U.S. Pat. Application Ser. No. 09/252,313, which claims priority of U.S. Provisional Pat. Application Ser. No. 60/075,321.

FIELD OF THE INVENTION

This invention relates to a series of pyridino arylpiperazine derivatives, pharmaceutical compositions containing them as well as methods of their use. The compounds of the invention selectively inhibit binding to the $\alpha 1_a$ adrenergic receptor, receptor which has been implicated in benign prostatic hyperplasia. In addition, compounds of the invention reduce intraurethral pressure in an in vivo model. As such the compounds are potentially useful in the treatment of this disease.

BACKGROUND

Benign prostatic hyperplasia (BPH), a nonmalignant enlargement of the prostate, is the most common benign tumor in men. Approximately 50% of all men older than 65 years have some degree of BPH and a third of these men have clinical symptoms consistent with bladder outlet obstruction (Hieble and Caine, 1986). In the U.S., benign and malignant diseases of the prostate are responsible for more surgery than diseases of any other organ in men over the age of fifty.

There are two components of BPH, a static and a dynamic component. The static component is due to enlargement of the prostate gland, which may result in compression of the urethra and obstruction to the flow of urine from the bladder. The dynamic component is due to increased smooth muscle tone of the bladder neck and the prostate itself (which interferes with emptying of the bladder) and is regulated by alpha 1 adrenergic receptors ($\alpha 1$-ARs). The medical treatments available for BPH address these components to varying degrees, and the therapeutic choices are expanding.

Surgical treatment options address the static component of BPH and include transurethral resection of the prostate (TURP), transurethral incision of the prostate (TUIP), open prostatectomy, balloon dilatation, hyperthermia, stents and laser ablation. TURP is the preferred treatment for patients with BPH and approximately 320,000 TURPs were performed in the U.S. in 1990 at an estimated cost of $2.2 billion (Weis et al., 1993). Although an effective treatment for most men with symptomatic BPH, approximately 20–25% of patients do not have a satisfactory long-term outcome (Lepor and Rigaud, 1990). Complications include retrograde ejaculation (70–75% of patients), impotence (5–10%), postoperative urinary tract infection (5–10%), and some degree of urinary incontinence (2–4%) (Mebust et al., 1989). Furthermore, the rate of reoperation is approximately 15–20% in men evaluated for 10 years or longer (Wennberg et al., 1987).

Apart from surgical approaches, there are some drug therapies which address the static component of this condition. Finasteride (Proscar®, Merck), is one such therapy which is indicated for the treatment of symptomatic BPH. This drug is a competitive inhibitor of the enzyme 5α-reductase which is responsible for the conversion of testosterone to dihydrotestosterone in the prostate gland (Gormley et al., 1992). Dihydrotestosterone appears to be the major mitogen for prostate growth, and agents which inhibit 5α-reductase reduce the size of the prostate and improve urine flow through the prostatic urethra. Although finasteride is a potent 5α-reductase inhibitor and causes a marked decrease in serum and tissue concentrations of dihydrotestosterone, it is only moderately effective in treating symptomatic BPH (Oesterling, 1995). The effects of finasteride take 6–12 months to become evident and for many men the clinical improvement is minimal (Barry, 1997).

The dynamic component of BPH has been addressed by the use of adrenergic receptor blocking agents ($\alpha 1$-AR blockers) which act by decreasing the smooth muscle tone within the prostate gland itself. A variety of $\alpha 1$-AR blockers (terazosin, prazosin, and doxazosin) have been investigated for the treatment of symptomatic bladder outlet obstruction due to BPH, with terazosin (Hytrin, Abbott) being the most extensively studied. Although the ($\alpha 1$-AR blockers are well-tolerated, approximately 10–15% of patients develop a clinically adverse event (Lepor, 1995). The undesirable effects of all members of this class are similar, with postural hypotension being the most commonly experienced side effect (Lepor et al., 1992). In comparison to the 5α-reductase inhibitors, the $\alpha 1$-AR blocking agents have a more rapid onset of action (Steers, 1995). However, their therapeutic effect, as measured by improvement in the symptom score and the peak urinary flow rate, is moderate. (Oesterling, 1995)

The use of $\alpha 1$-AR antagonists in the treatment of BPH is related to their ability to decrease the tone of prostatic smooth muscle, leading to relief of the obstructive symptoms. Adrenergic receptors are found throughout the body play a dominant role in the control of blood pressure, nasal congestion, prostrate function and other processes (Harrison et al., 1991). However, there are a number of cloned $\alpha 1$-AR receptor subtypes: $\alpha 1_a$-AR, $\alpha 1_b$-AR and $\alpha 1_d$-AR (Bruno et al., 1991; Forray et al., 1994; Hirasawa et al., 1993; Ramarao et al., 1992; Schwinn et al., 1995; Weinberg et al., 1994). A number of labs have characterized the $\alpha 1$-ARs in human prostate by functional, radioligand binding, and molecular biological techniques (Forray et al., 1994; Hatano et al., 1994; Marshall et al., 1992; Marshall et al., 1995; Yamada et al., 1994). These studies provide evidence in support of the concept that the $\alpha 1_a$-AR subtype comprises the majority of $\alpha 1$-ARs in human prostatic smooth muscle and mediates contraction in this tissue. These findings suggest that the development of a subtype-selective $\alpha 1a$-AR antagonist might result in a therapeutically effective agent with reduced side effects for the treatment of BPH.

SUMMARY OF THE INVENTION

The compounds of this invention selectively bind to the $\alpha 1_a$-AR receptor, antagonize the activity of said receptor and are selective for prostate tissue over aortic tissue. As such, these represent a viable treatment for BHP without the side effects associated with known $\alpha 1$-AR antagonists.

The invention includes compounds of Formula I

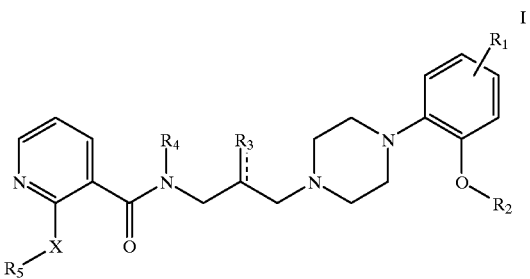

wherein:
R$_1$ is hydrogen, halogen, C$_{1-5}$alkoxy, hydroxyl, or C$_{1-5}$alkyl;
R$_2$ is C$_{1-6}$alkyl, substituted C$_{1-6}$alkyl
  where the alkyl substituents are independently selected from one or more halogens,
  phenyl, substituted phenyl
  where the phenyl substituents are independently selected from one or more members of the group consisting of C$_{1-5}$alkyl, C$_{1-5}$alkoxy, and trihaloC$_{1-5}$alkyl,
  phenylC$_{1-5}$alkyl, or substituted phenylC$_{1-5}$alkyl
  where the phenyl substituents are independently selected from one or more members of the group consisting of C$_{1-5}$alkyl, halogen, C$_{1-5}$alkoxy, and trihaloC$_{1-5}$alkyl;
R$_3$ is hydrogen, hydroxy or C$_{1-5}$alkoxy if the hashed line is absent or is oxygen if the hashed line is present;
R$_4$ is hydrogen, C$_{1-5}$alkyl, phenylC$_{1-5}$alkyl or substituted phenylC$_{1-5}$alkyl
  where the phenyl substitutents are independently selected from one or more members of the group consisting of C$_{1-5}$alkyl, C$_{1-5}$alkoxy, and trihaloC$_{1-5}$alkyl;
R$_5$ is C$_{1-6}$alkyl, substituted C$_{1-6}$alkyl
  where the alkyl substitutents are independently selected from one or more halogens,
  phenyl, substituted phenyl
  where the phenyl substitutents are independently selected from one or more members of the group consisting of C$_{1-8}$alkyl, hydrogen, halogen, hydroxy, C$_{1-8}$alkyl,
  substituted C$_{1-8}$alkyl
    where the alkyl substituents are independently selected from one or more halogens,
    C$_{1-5}$alkoxy, amino, C$_{1-5}$alkylamino, diC$_{1-5}$alkylamino, C$_{1-5}$alkylcarbonyl, C$_{1-5}$alkoxycarbonyl, arylcarbonyl, nitrile, aminosulfonyl, C$_{1-5}$alkylsulfonyl, phenylsulfonyl, and substituted phenyisulfonyl
      where the phenyl substituents are independently selected from one or more members of the group consisting of C$_{1-8}$alkyl hydrogen, halogen, hydroxy and nitro;
  phenylC$_{1-5}$alkyl, substituted phenylC$_{1-5}$alkyl
  where the phenyl substitutents are independently selected from one or more members of the group consisting of C$_{1-8}$alkyl hydrogen, halogen, hydroxy, C$_{1-8}$alkyl, substituted C$_{1-8}$alkyl
    where the alkyl substitutents are independently selected from one or more halogens,
    C$_{1-5}$alkoxy, amino, C$_{1-5}$alkylamino, diC$_{1-5}$alkylamino, C$_{1-5}$alkylcarbonyl, C$_{1-5}$alkoxycarbonyl, and nitro;

X is oxygen, sulfur or NH;
pharmaceutically acceptable salts thereof;
and stereoisomers, racemic mixtures, as well as enantiomers thereof.

In addition this invention contemplates pharmaceutical compositions containing an effective dose of compounds of Formula I. Still further this invention contemplates methods of treating diseases associated with the α-1$_a$ adrenergic receptor consisting of administering an effective dose of a compound of Formula I to a mammal. This invention also contemplates a method of treating benign prostatic hyperplasia consisting of administering an effective dose of a compound of Formula I to a mammal.

DETAILED DESCRIPTION OF THE INVENTION

The terms used in describing the invention are commonly used and known to those skilled in the art. However, the terms that could have other meanings are defined. "HBSS" refers to Hank's Balanced Salt Solution. "Independently" means that when there are more than one substituent, the substitutents may be different. The term "alkyl" refers to straight, cyclic and branched-chain alkyl groups and "alkoxy" refers O-alkyl where alkyl is as defined supra. "DMAP" refers to dimethylaminopyridine, "HOBT" refers to hydroxybenzotriazole hydrate, and "EDCI" refers to 1-(3-dimethylaminopropyl)-3-ethylcarbodiimide hydrochloride. The term "HATU" refers to O-(7-azabenzotriazol-1-yl)-1,1,3,3-tetrametyluronium hexafluorophosphate and the symbol "Ph" refers to phenyl, and "aryl" includes mono and fused aromatic rings such as phenyl and naphthyl. The symbol "ES" refers to electrospray and the symbol "MS" refers to mass spectrum. Some of the compounds of Formula I include a chiral carbon atom. Therefore those compounds may be prepared as stereoisomers, racemic mixtures or pure enantiomers. All stereoisomers, pure enantiomers and racemic mixtures are considered to be within the scope of this invention.

The compounds of the invention may be prepared by the following schemes, where some schemes produce more than one embodiment of the invention. In those cases, the choice of scheme is a matter of discretion which is within the capabilities of chemists.

A compound of Formula I where X is NH, R$_1$ is hydrogen, R$_2$ is phenyl, R$_3$ is hydroxy, R$_4$ is hydrogen, and R$_5$ is 3-trifluoromethylphenyl may be prepared using Scheme 1. 1-Azido-3-(p-toluenesulfonyloxy)propan-2-ol 1a, is heated at about 100° C. with an appropriately substituted piperazine derivative, 1b for about 2–5 days to give the azide 1c. This azide is treated with Pd/C and H$_2$ (50 psi) in an inert solvent over 16 h to give the free amine 1d. This amine is treated with a 3-acyl-2-substituted pyridine derivative, such as 2-[(3-trifluoromethylphenyl)amino]-3-pyridinecarbonyl chloride, 1e, DMAP and N,N-diisopropylethylamine in methylene chloride at about room temperature for 2–16 h to give the desired compound of Formula I. This scheme may be used to prepare a number of compounds of Formula I. For example, to prepare compounds where R$_1$ and R$_2$ vary, simply replace the illustrated 1b with any known substituted piperazines. Although the illustrated product was prepared from the racemic azide 1a, the pure enantiomers of this azide are known and can be used in this scheme. To prepare compounds where R$_5$ is other than substituted phenyl, replace the acyl pyridine derivative 1e with another acyl pyridine. For example to prepare a compound where R$_5$ is phenylmethyl, replace the illustrated 1e with 2-[(phenylmethyl)amino]-3-pyridinecarbonyl chloride. To prepare compounds where X is other than NH, replace the amino substituted acylpyridine with a thio or an oxy substituted pyridine. For example to prepare a compound where X is sulfur, $R_1$ is hydrogen, $R_2$ is phenyl, $R_3$ is hydroxy, $R_4$ is hydrogen, and $R_5$ is phenyl, replace the illustrated 1e with 2-(phenylthio)pyridine-3-carboxylic acid chloride.

To prepare compounds where $R_3$ is $C_{1-5}$alkoxy replace starting material 1c with 1-[1-azido-2-methoxypropan-1-yl]-4-[2-isopropoxyphenyl]piperazine and carry out the remaining steps of the scheme.

Compounds where $R_3$ is carbonyl may be prepared by treating the products of Scheme 1 with an oxidizing agent such as the Swern's reagent (formed from oxalyl chloride and DMSO) at −78° C. to room temperature over 30 min to 1 h.

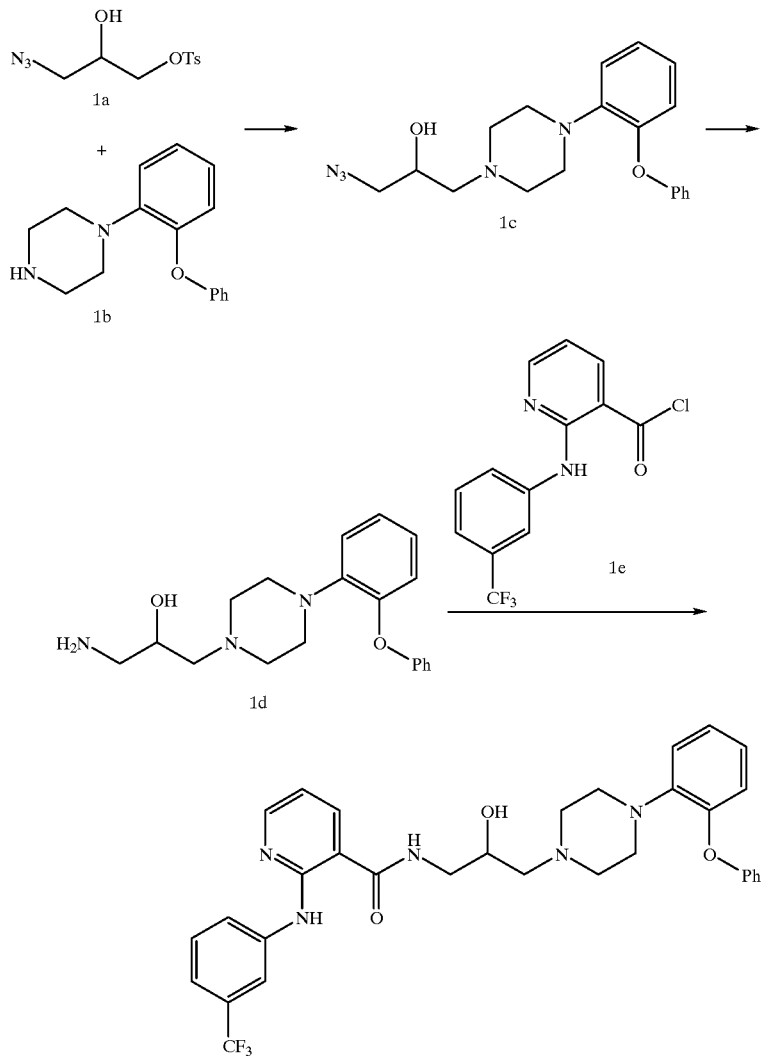

Scheme 1

Scheme 2 may be used to prepare compounds of Formula I where X is sulfur, $R_1$ is fluoro, $R_2$ is ethyl, $R_3$ is hydrogen, $R_4$ is hydrogen, and $R_5$ is 4-chlorophenyl. An appropriately substituted piperazine derivative 2a is treated with N-BOC protected 3-bromopropylamine and cesium carbonate in acetonitrile at reflux for 16 h to give the substituted piperazine derivative 2b. This derivative is converted to the free amine, 2c, by treatment with TFA and methylene chloride at room temperature over 2–6 h. Derivative 2c is coupled with a substituted acyl pyridine derivative 2d using DMAP, and N,N-diisopropylethylamine in methylene chloride at about room temperature for 2–6 h to give the desired compound of Formula I. As described in Scheme 1, Scheme 2 may be modified to give many compounds of Formula I.

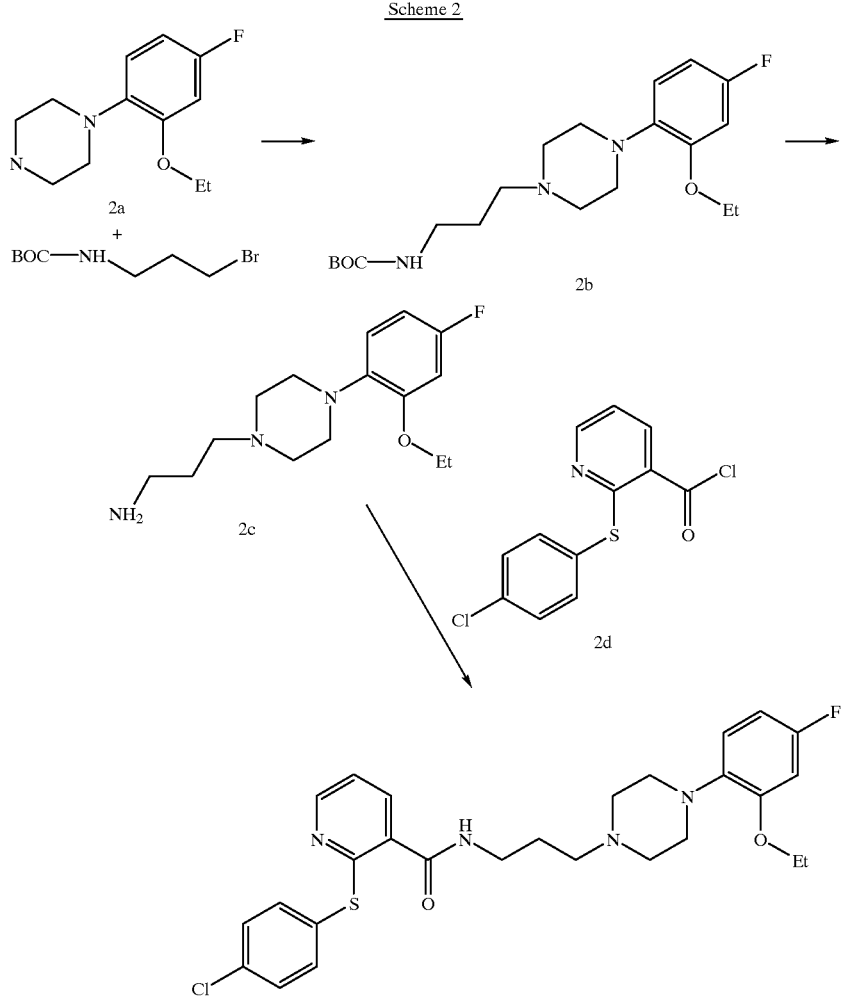

Scheme 2

Another method of preparing compounds of the invention is illustrated by Scheme 3. Treatment of derivative 2c and 2-chloronicotinic acid with HOBT, DMAP, EDCI and N,N-diisopropylethylamine in methylene chloride at about room temperature for 2–6 h gives the chloropyridine 3a. Treatment of this derivative with an aromatic alcohol such as 3b gives a compound of the invention where X is oxygen, $R_1$ is fluoro, $R_2$ is ethyl, $R_3$ is hydrogen, $R_4$ is hydrogen, and $R_5$ is 4-methylphenyl.

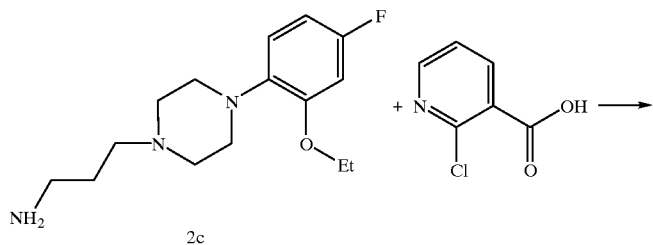

Scheme 3

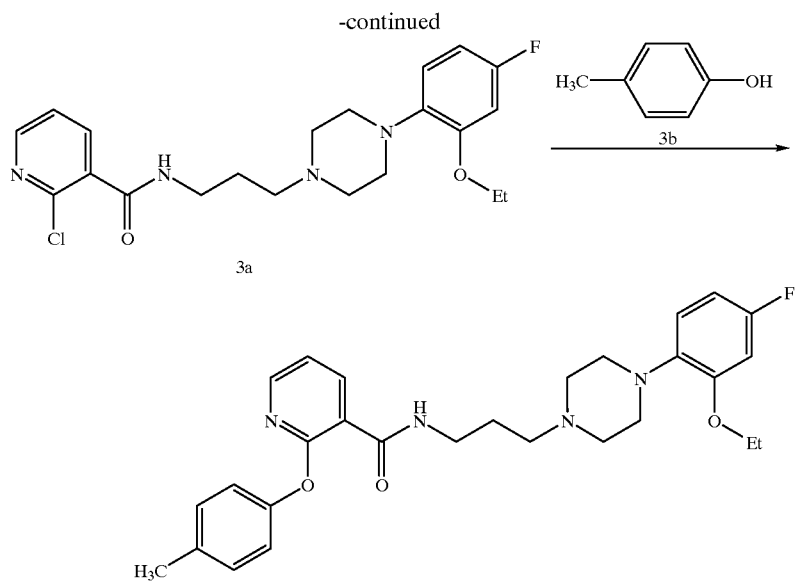

To produce compounds of the invention where $R_4$ is other than hydrogen, Scheme 4 may be used. The amino group of intermediates 2c may be treated with an aldehyde 4a such as benzaldehyde to give the imine 4b. This intermediate may be reduced with $NaBH_4$ at room temperature to give the monoamine 4c. This amine is coupled with a substituted acyl pyridine derivative, using DMAP and N,N-diisopropylethylamine in methylene chloride at about room temperature for 2–6 h to give the desired compound of Formula I. As described in previous schemes, Scheme 4 may be modified to give a number of compounds of Formula I. For example, to produce a compound where $R_3$ is hydroxy, replace 2c with intermediate 1d and follow the remaining steps of Scheme 4.

Scheme 4

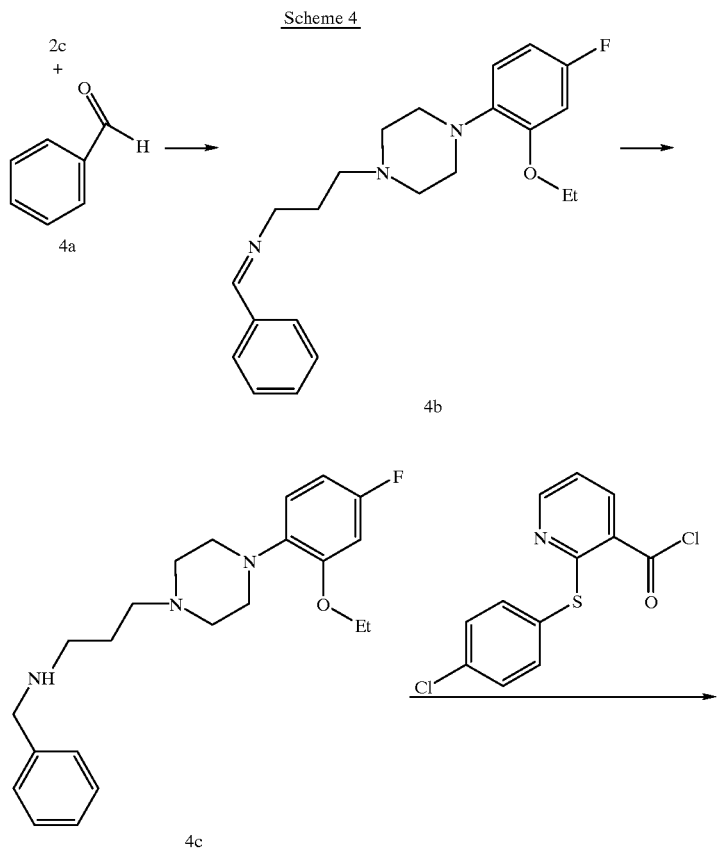

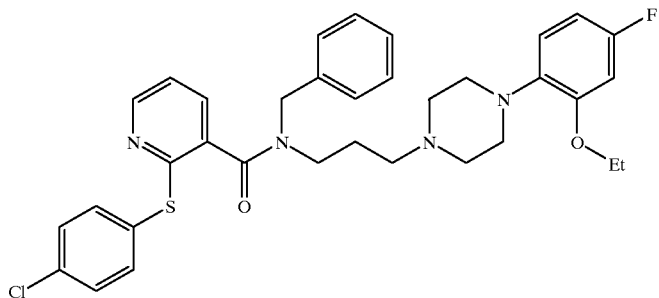

To produce pure enantiomers of compounds of Formula I where $R_3$ is hydroxy, Scheme 5 may be used. (S)(+) epichlorohydrin (97% ee) may be treated with benzylamine in a suitable organic solvent such as hexane at about room temperature for about 48–72 hours to give hydroxy compound 5a. This intermediate may be treated with a BOC reagent agent such as di-tert-butyl dicarbonate, and an organic base such as triethylamine in an inert solvent such as THF at about 0° C. to about room temperature over 10 to 24 h to give the N-protected derivative 5b. This intermediate may be treated with piperazine derivative, 5c, a base such as potassium hydroxide, in an alcoholic solvent such as methanol at about 0° C. to about room temperature over about 1 to about 3 days to give the coupled derivative 5d. This compound may be deprotected by treatment with an acid such as TFA at about room temperature over 18–24 h to give free amine 5e. This amine may be debenzylated with using a palladium catalyst and ammonium formate in an alcoholic solvent such as EtOH at about 45–60° C. over 20 h to give the primary amine 5f. This amine may be coupled to acids of type 5g using peptide coupling agents such as HATU to give a compound of Formula I. As described in Scheme I, Scheme 5 may be modified to give a number of compounds of Formula I.

Scheme 5

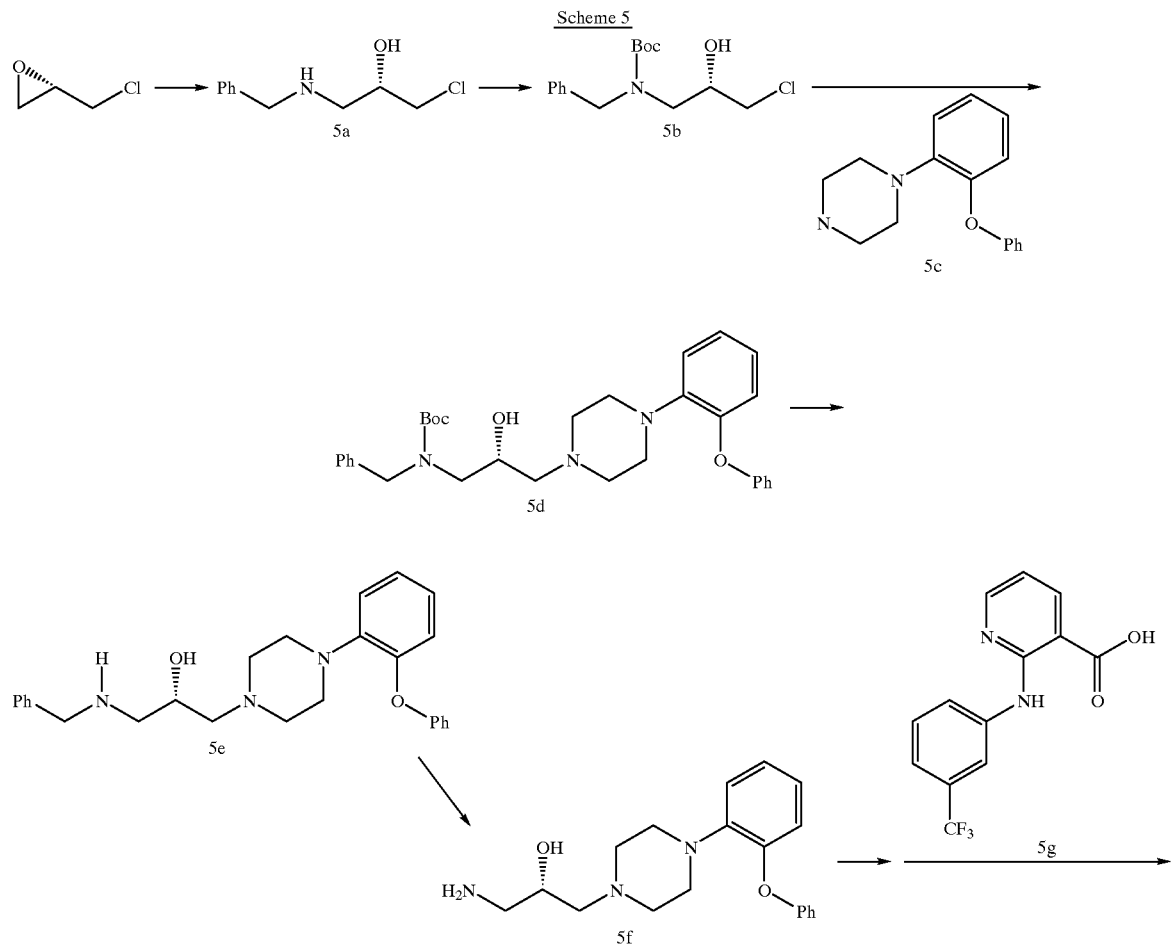

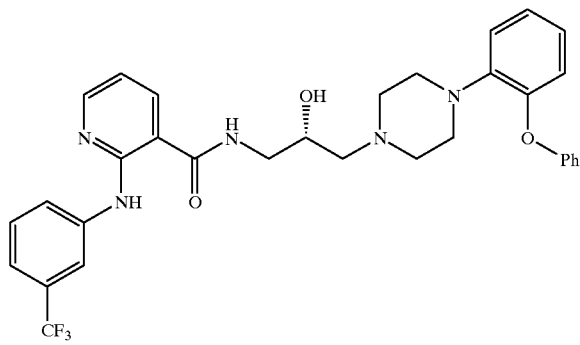

Although the claimed compounds are useful as antagonists of α1$_a$-AR, some compounds are more active than others and are either preferred or particularly preferred. The preferred compounds of the invention include compounds where:

$R_1$ is halogen or hydroxy,
$R_2$ is phenyl or hydrogen,
$R_3$ is $C_{1-5}$alkoxy,
$R_4$ is $C_{1-5}$alkyl,
$R_5$ is $C_{1-5}$alkyl, and
X is sulfur The particularly preferred compounds of Formula I include compounds where:

$R_1$ is hydrogen,
$R_2$ is $C_{1-6}$alkyl
$R_3$ is hydroxy or hydrogen
$R_4$ is hydrogen,
$R_5$ is phenyl and $C_{1-5}$alkyl-substituted phenyl
X is oxygen As indicated by the biological activity, the compounds of Formula I may be used in pharmaceutical compositions to treat patients (humans and other mammals) with disorders related to inhibiting the activity of the α1$_a$ adrenergic receptor. The preferred route is oral administration, however compounds Oral doses range from about 0.01 to about 100 mg/kg daily; where the optimal dose range is about 0.1 to about 25 mg/kg/per day. Infusion doses can range from about 0.001–1 mg/kg/min of inhibitor, admixed with a pharmaceutical carrier over a period ranging from several minutes to several days may be administered by intravenous infusion.

The pharmaceutical compositions can be prepared using conventional pharmaceutical excipients and compounding techniques. Oral dosage forms may be elixirs, syrups, capsules tablets and the like. Where the typical solid carrier is an inert substance such as lactose, starch, glucose, methyl cellulose, magnesium sterate, dicalcium phosphate, mannitol and the like; and typical liquid oral excipients include ethanol, glycerol, water and the like. All excipients may be mixed as needed with disintegrants, diluents, granulating agents, lubricants, binders and the like using conventional techniques known to those skilled in the art of preparing dosage forms. Parenteral dosage forms may be prepared using water or another sterile carrier.

Typically the compounds of Formula I are isolated and used as free bases, however the compounds may be isolated and used as their pharmaceutically acceptable salts. Examples of such salts include hydrobromic, hydroiodic, hydrochloric, perchloric, sulfuric, maleic, fumaric, malic, tartatic, citric, benzoic, mandelic, methanesulfonic, hydroethanesulfonic, benzenesulfonic, oxalic, pamoic, 2-naphthalenesulfonic, p-toluenesulfonic, cyclohexane-sulfamic and saccharic.

In order to illustrate the invention the following examples are included. These examples do not limit the invention. They are meant only to suggest a method of practicing the invention. Those knowledgeable in the treatment of benign prostatic hyperplasia, chemical synthesis, pharmaceutical compounding as well as other specialties, may find other methods of practicing the invention. However those methods are deemed to be within the scope of this invention.

PREPARATIVE EXAMPLES

Example 1

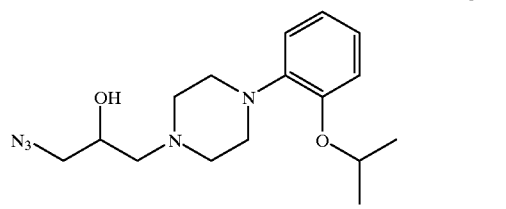

Cpd. 1

The fumarate salt of 1-(2-isopropoxyphenyl)-piperazine (3.91 g, 12 mmol) was basified with 20% NaOH$_{(aq)}$ (100 mL) and extracted with methylene chloride. The combined organic layers were dried (Na$_2$SO$_4$) and concentrated to give an oil (2.74 g). A mixture of the oil and 1-azido-3-(p-toluenesulfonyloxy)propan-2-ol (3.25 g, 12 mmol, Antonin Holy, *Collect. Czech. Chem. Comm.* 1989, 54(2), 446) was stirred at 100° C. for 36 h. The cooled mixture was diluted with water and extracted with ether, dried (Na$_2$SO$_4$) and concentrated. The product was purified by column chromatography (silica gel) to yield compound 1 as (2.92 g, 76%) as a light-brown solid: MS (ES) m/z: 320 (MH$^+$); Anal. Calcd for C$_{16}$H$_{25}$N$_5$O$_2$: C, 60.17; H, 7.89; N, 21.93. Found: C, 60.45; H, 7.83; N, 22.01.

Example 2

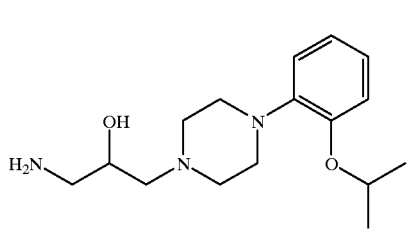

Cpd. 2

10% HCl (6 mL) was added to a mixture of compound 1 (2.43 g, 7.6 mmol) and 10% Pd/C (1.22 g) in MeOH (60 mL) and the mixture was hydrogenated under $H_2$ (50 psi) in a Parr shaker for 16 h at 20° C. The mixture was filtered through celite and the filtrate was concentrated. The residue was basified with 20% NaOH and extracted with methylene chloride. The combined organic layers were dried ($Na_2SO_4$) and concentrated to yield compound 2 as a yellowish oil (2.2 g, 95%): MS (ES) m/z: 294 ($MH^+$).

Example 3

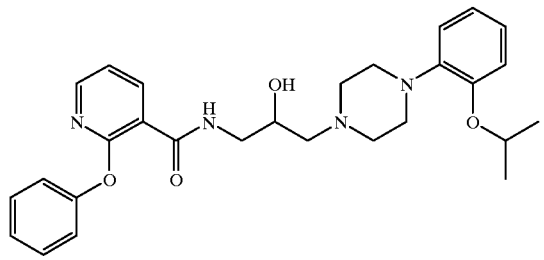

Cpd. 3

A mixture of compound 2 (100 mg, 0.341 mmol), 2-phenoxypyridine-3-carbonyl chloride (81 mg, 0.341 mmol), DMAP (cat.) and N,N-diisopropylethylamine (0.23 mL) in methylene chloride (2 mL) was stirred at 20° C. for 16 h. The mixture was concentrated, diluted with water and extracted with EtOAc. The combined organic layer was dried ($Na_2SO_4$) and concentrated. The product was purified by column chromatography (silica gel) to yield 116 mg (69%) of compound 3 as a foam: $^1H$ NMR (300 MHz, $CDCl_3$) δ 8.59 (d, J=6.3 Hz, 1 H), 8.32 (brs, 1 H), 8.20 (d, J=3.1 Hz, 1 H), 7.44 (m, 2 H), 7.21 (m, 4 H), 6.87 (m, 4 H), 4.57 (m, 1 H), 3.98 (m, 1 H), 3.75 (m, 1 H), 3.5 (m, 1 H), 3.06 (m, 4 H), 2.79 (m, 2 H), 2.48 (m, 4 H), 1.33 (d, J=5.9 Hz, 6 H); MS (ES) m/z: 491($MH^+$).

Example 4

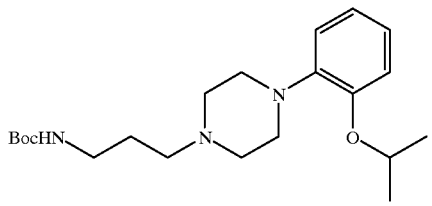

Cpd. 4

3-Bromopropylamine hydrobromide (5 g, 22.8 mmol) was dissolved in 10%NaOH (50 mL), extracted with methylene chloride and concentrated. To the free base in methylene chloride was added $(Boc)_2O$ (5.23 g, 23.9 mmol) and this mixture was stirred at 20° C. for 4 h. The methylene chloride layer was washed with $H_2O$, diluted citric acid (6%), $NaHCO_3$ and sat NaCl solution, dried and concentrated. The product was purified by column chromatography (silica gel) to yield the protected amine (4.84 g, 89%). The fumarate salt of 1-(2-isopropoxyphenyl)-piperazine (5.1 g, 15 mmol) was basified with 20% $NaOH_{(aq)}$ (100 mL), extracted with methylene chloride, dried ($Na_2SO_4$) and concentrated to give a yellow oil (3.15 g). A mixture of the oil, the protected amine (3.42 g, 14.3 mmol), and $Cs_2CO_3$ (4.66 g, 14.3 mmol) in $CH_3CN$ (50 mL) was heated at reflux overnight. The solid was filtered off and the filtrate was evaporated. The product was purified by column chromatography (silica gel) to yield compound 4(4.4 g, 81%): MS (ES) m/z: 378($MH^+$).

Example 5

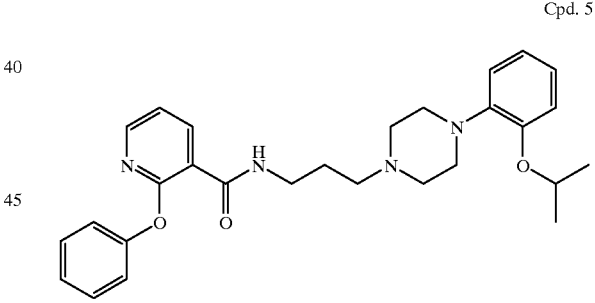

Cpd. 5

Compound 4 (0.185 g, 0.53 mmol), was dissolved in 25% TFA/methylene chloride (5 mL) and stirred for 1.5 h. The solvent was removed and the TFA salt was washed with toluene(3x) and then basified with 20% $NaOH_{(aq)}$ followed by extracted with methylene chloride (3x), dried ($Na_2SO_4$) and concentrated to give a oil. This oil was dissolved in methylene chloride (4 mL), diisopropylethyl amine (0.34 g, 2.64 mmol), catalytic amount of DMAP and 2-phenoxypyridine-3-carbonyl chloride (0.12 g, 0.53 mmol). The reaction was stirred at 20° C. under $N_2$ for 2 h and concentrated. The product was purified by column chromatography (silica gel) to yield compound 5 (0.2 g, 80%): $^1H$ NMR (300 MHz, $CDCl_3$) δ 8.61 (dd, J=7.5, 2.0 Hz, 1 H), 8.20 (dd, J=4.9, 2.0 Hz, 1 H), 8.05 (m, 1 H), 7.46 (m, 2H), 7.29 (d, J=7.4 Hz, 1H), 7.15 (m, 3H), 6.88 (m, 4H), 4.56 (m, 1H), 3.59 (q, J=6.3 Hz, 2H), 3.03 (m, 4H), 2.56 (m, 4H), 2.49 (t, J=7.0 Hz, 2H), 1.87 (m, 2H), 1.32 (d, J=6.1 Hz, 6H); MS (ES) m/z: 475 (MH⁺).

Example 6

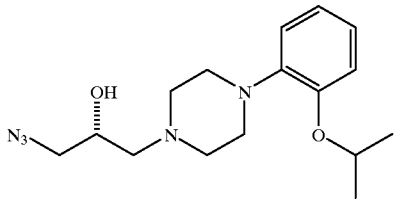

Cpd. 6

The fumarate salt of 1-(2-isopropoxyphenyl)-piperazine (112.5 g, 345 mmol) was basified with 20% NaOH$_{(aq)}$ (500 mL), extracted with methylene chloride (3×), dried (Na$_2$SO$_4$), and concentrated to give about 70 g oil. A mixture of the oil and (2S)-3-azido-2-hydroxypropyl p-toluenesulfonate (91 g, 335 mmol, Kristina Juricova, *Collect. Czech. Chem. Comm.* 1995, 60, 237) was stirred at 100° C. in NMP with triethylamine (70 g, 690 mmol) for 30 h. The mixture was cooled, diluted with water and extracted with ether (3×500 mL). The combined extracts were back washed with NaCll (sat) (100 mL), dried (Na$_2$SO$_4$) and concentrated. The product was purified by column chromatography (silica gel) and recrystallization (methylene chloride/hexanes) to yield 70.6 g (66%) of compound 6 (98.8% ee assay by chiralcel AD column) as a off-white: [α]$^{25}_D$ −3.6° (c=1, CH$_3$OH); ¹H NMR (300 MHz, CDCl$_3$) δ 6.91 (m, 4 H), 4.59 (m, 1 H), 3.93 (m, 1 H), 3.67 (brs, 1 H), 3.42 (dd, J=12.6, 3.8 Hz, 1 H), 3.23 (dd, J=12.6, 5.4 Hz, 1 H), 3.12 (m, 4 H), 2.83 (m, 2 H), 2.53 (m, 3 H), 2.42 (dd, J=12.2, 3.8 Hz, 1 H), 1.34 (d, J=6.0 Hz, 6 H); MS (ES) m/z: 320 (MH⁺).

Example 7

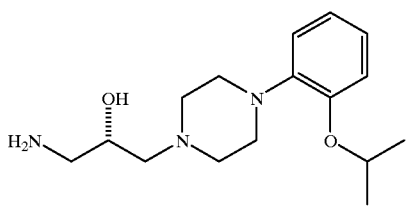

Cpd. 7

10% HCl (6 mL), was added to a mixture of compound 6 (15 g, 47 mmol) and 10% Pd/C (4 g) in MeOH (100 mL). The mixture was hydrogenated under H$_2$ (50 psi) in a Parr shaker for 21 h at 20° C. The mixture was filtered through celite and the filtrate was concentrated. The residue was basified with 20% NaOH$_{(aq)}$ (75 mL), extracted with methylene chloride (3×), dried (Na$_2$SO$_4$), and concentrated to yield compound 7 (14 g, ~100%) as a yellowish oil: [α]$^{25}_D$ +23.6° (c=1, CHCl$_3$); ¹H NMR (300 MHz, CDCl$_3$) δ 6.91 (m, 4 H), 4.59 (m, 1 H), 3.76 (m, 1 H), 3.12 (m, 4 H), 2.83 (dd, J=12.7, 3.7 Hz, 2 H), 2.82 (m, 1 H), 2.25–2.68 (m, 8 H), 1.34 (d, J=6.1 Hz, 6 H); MS (ES) m/z: 294 (MH⁺).

Example 8

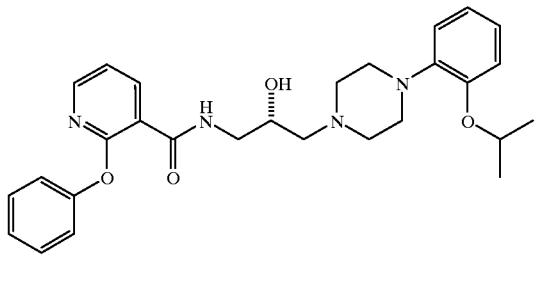

Cpd. 8

Piperazine 7 (8 g, 27.3 mmol) was dissolved in a mixture of diisopropylethylamine (14.1 g, 109.2 mmol) and methylene chloride (100 mL). The resulting light-yellowish solution was added slowly into a solution of methylene chloride (50 mL), 2-phenoxynicotinic acid (5.87 g, 27.3 mmol), EDCl (5.24 g, 27.3 mmol), HOBT (3.69 g, 27.3 mmol) and DMAP (50 mg, cat.) at 20° C. and stirred for 18 h. Water was added and the resulting mixture was extracted with ether (3×). The combined organic extracts were washed with NaCl$_{(sat)}$, dried (Na$_2$SO$_4$) and concentrated. The product was purified by column chromatography (SiO$_2$, methylene chloride/acetone) to yield compound 8 (8.4 g, 62%) as a white foam: [α]$^{25}_D$ +14.8° (c=1, CHCl$_3$); ¹H NMR (300 MHz, CDCl$_3$) δ 8.60 (dd, J=7.5, 2 Hz, 1 H), 8.31 (brs, 1 H), 8.22 (dd, J=4.7, 2 Hz, 1 H), 7.43 (brt, J=7.7 Hz, 2 H), 7.14–7.30 (m, 4 H), 6.87 (m, 4 H), 4.58 (m, 1 H), 3.97 (m, 1 H), 3.75 (m, 1 H), 3.51 (m, 1 H), 3.06 (m, 4 H), 2.80 (m, 2 H), 2.49 (m, 4 H), 1.33 (d, J=6.0 Hz, 6 H); MS (ES) m/z: 491 (MH⁺).

Example 9

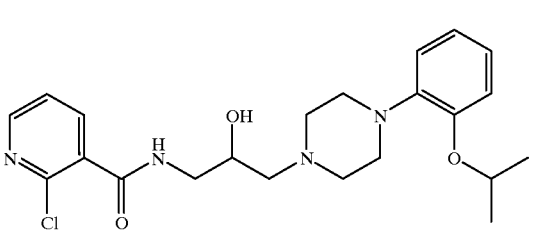

Cpd. 9

A mixture of compound 2 (900 mg, 3.07 mmol), 2-chloronicotic acid (485 mg, 3.07 mmol), EDCl (589 mg, 3.07 mmol), HOBT (414 mg, 3.07 mmol), DMAP (cat.) and N,N-diisopropylethylamine (2 mL) in methylene chloride (20 mL) was stirred at 20° C. for 20 h. The mixture was concentrated, diluted with water and extracted with ether. The organic layer was dried (Na$_2$SO$_4$) and concentrated. The product was purified by column chromatography (silica gel) to yield 580 mg (44%) of compound 9 as a white foam: MS (ES) m/z: 433 (MH⁺).

Example 10

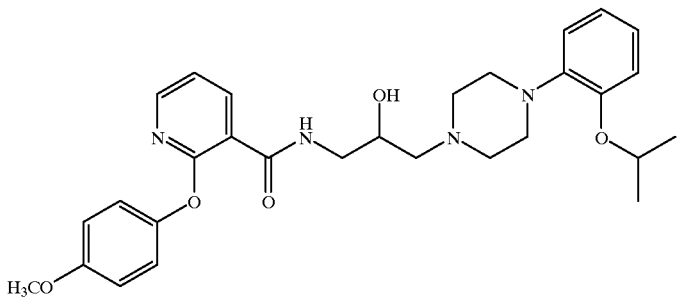

Cpd. 10

A mixture of compound 9 (43 mg, 0.1 mmol), 4-methoxyphenol (124 mg, 1 mmol) and cesium carbonate (65 mg, 0.2 mmol) in NMP (1 mL) was stirred at 110° C. for 20 h. The resulting mixture was cooled, water was added and this mixture was extracted with ether. The extract was dried (Na$_2$SO$_4$) and concentrated. The product was purified by column chromatography (silica gel) to yield compound 10 (36 mg, 69%) as a white foam: MS (ES) m/z: 521 (MH$^+$).

Example 11

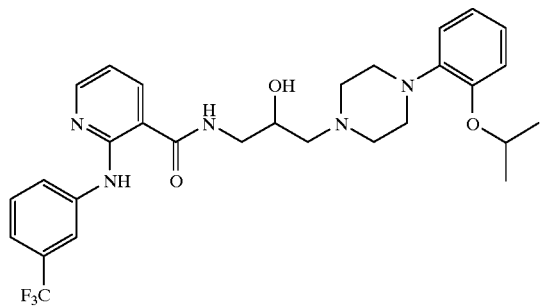

Cpd. 11

A mixture of compound 2 (100 mg, 0.341 mmol), niflumic acid (96 mg, 0.341 mmol), EDCl (65 mg, 0.341 mmol), HOBT (46 mg, 0.34 mmol), DMAP (cat.) and N,N-diisopropylethylamine (0.23 mL) in methylene chloride (2 mL) was stirred at 20° C. for 20 h. The mixture was concentrated. The product was purified by column chromatography (silica gel) to yield compound 11 (101 mg, 53%) as a foam: MS (ES) m/z: 558 (MH$^+$).

Example 12

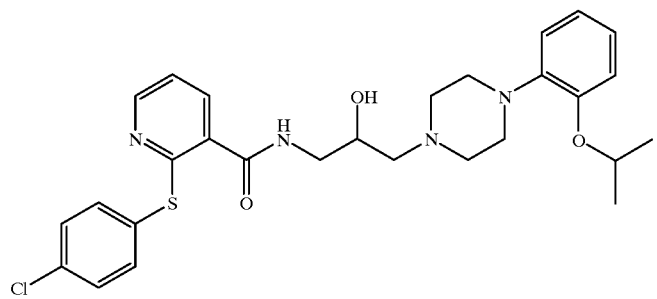

Cpd. 12

A mixture of compound 2 (100 mg, 0.341 mmol), 2-(4-chlorophenylthio)pyridine-3-carboxylic acid (91 mg, 0.341 mmol), EDCl (65 mg, 0.341 mmol), HOBT (46 mg, 0.34 mmol), DMAP (cat.) and N,N-diisopropylethylamine (0.23 mL) in methylene chloride (2 mL) was stirred at 20° C. for 20 h. The mixture was concentrated. The product was purified by column chromatography (silica gel) to yield compound 12 (128 mg, 70%) as a foam: MS (ES) m/z: 541 (MH$^+$).

Example 13

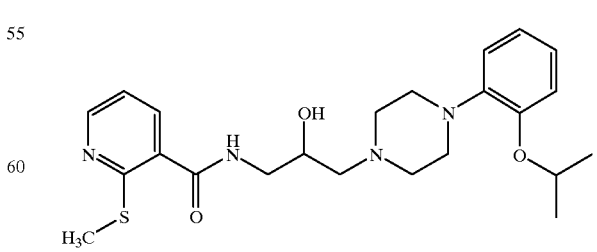

Cpd. 13

A mixture of compound 2 (100 mg, 0.341 mmol), 2-methoxynicotinic acid (52 mg, 0.341 mmol), EDCl (65 mg, 0.341 mmol), HOBT (46 mg, 0.34 mmol), DMAP (cat.) and N,N-diisopropylethylamine (0.23 mL) in methylene chloride (2 mL) was stirred at 20° C. for 20 h. The mixture was concentrated. 3% $K_2CO_{3(aq)}$ was added and extracted with ether, dried ($Na_2SO_4$) and concentrated. The product was purified by column chromatography (silica gel) to yield compound 13 (32 mg, 22%) as a foam: MS (ES) m/z: 429 (MH+).

Example 14

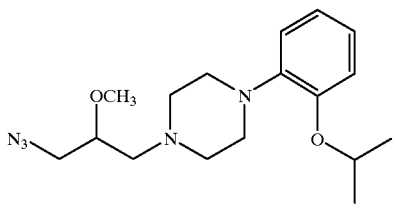

Cpd. 14

Compound 1 (0.8 g, 2.5 mmol) was dissolved in 50 mL of anhydrous THF. The solution was cooled to 0° C. and 2 eq of 60% NaH (0.2 g, 5.0 mmol) was added. The solution was stirred for 10 min and 1.5 eq of $CH_3I$ (0.53 g, 3.8 mmol) was added. The reaction mixture was stirred at 0° C. for 2 h. NaH (0.1 g, 2.5 mmol) and 1 eq of $CH_3I$ (0.15 mL) were added and the mixture was stirred for another 2 h. The reaction was quenched with sat $NH_4Cl$, the solvent was evaporated, and the aqueous layer was washed with methylene chloride (3x), dried ($Na_2SO_4$) and concentrated. The product was purified by column chromatography (silica gel) to yield of compound A (0.69 g, 83%): MS (ES) m/z: 334 (MH+).

Example 15

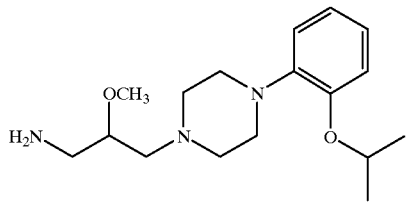

Cpd. 15

10%HCl (0.3 mL) was added to a mixture of compound 14 (0.64 g, 1.9 mmol) and 10% Pd/C (0.13 g) in MeOH (5 mL) and the mixture was hydrogenated under $H_2$ (50 psi) in a Parr shaker overnight. The mixture was filtered through celite and the filtrate was concentrated. The residue was basified with 20% NaOH and extracted with methylene chloride (3x). The combined organic extract were dried ($Na_2SO_4$) and concentrated to give a yellow oil at quantitative yield. MS (ES) m/z: 308 (MH+).

Example 16

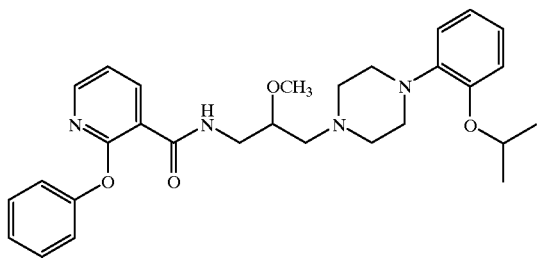

Cpd. 16

Compound 15 (0.15 g, 0.49 mmol) was dissolved in methylene chloride (4 mL) and diisopropylethyl amine (0.25 g, 1.95 mmol) was added. To this solution was added a mixture of HATU (0.185 g, 0.49 mmol) and 2-phenoxynicotinic acid (0.11 g, 0.49mmol). The reaction was stirred under $N_2$ overnight at RT, the solvent was evaporated and the residue was dissolved in EtOAc. This solution was washed with 3% $K_2CO_3$, the organic layer was dried ($Na_2SO_4$) and concentrated. The product was purified by flash chromatography ($SiO_2$, methylene chloride/acetone=10:1, 8:1, 6;1 4:1) to yield compound 16 (0.16 g, 64%) as an oil: $^1$H NMR (300 MHz, $CDCl_3$) δ 8.61 (dd, J=7.4 Hz, 1 H), 8.27 (brs, 1 H), 8.23 (m, 1 H), 7.44 (m, 2 H), 7.26 (m, 1 H), 7.17 (m, 3 H), 6.87 (m, 4 H), 4.58 (m, 1 H), 3.92 (m, 1 H), 3.55 (m, 2 H), 3.42 (s, 3 H), 3.03 (brs, 4 H), 2.54 (m, 6 H), 1.33 (d, J=6.0 Hz, 6 H); MS (ES) m/z: 308 (MH+).

Example 17

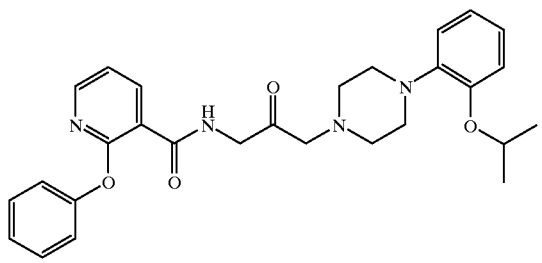

Cpd. 17

Oxalyl chloride (0.03 g, 0.22 mmol) was dissolved in 0.3 mL of methylene chloride. A mixture of DMSO (0.035 mL, 0.49 mmol) in methylene chloride (3.0 mL) was added dropwise to this solution at −78° C. The mixture was stirred at −78° C. for 1 h. A solution of compound 3 (68414, 0.1 g, 0.2 mmol) in methylene chloride (0.4 mL) was added slowly. The reaction mixture was stirred for 30 min and TEA (0.14 mL, 1.02 mmol) was added slowly. The mixture was allowed to warm up to room temperature, water was added and the resulting mixture was extracted with methylene chloride. The combined organic layers were dried ($Na_2SO_4$) and concentrated to give compound 17 (13.2 mg, 13%): $^1$H NMR (300 MHz, $CDCl_3$) δ 8.69 (brs, 1 H), 8.61 (dd, J=7.6 Hz, 1 H), 8.23 (dd, J=4.6 Hz, 1 H), 7.46 (m, 2 H), 7.28 (m, 3 H), 7.15 (m, 1 H), 6.89 (m, 4 H), 4.57 (m, 3H), 3.35 (s, 2

H), 3.15 (brs, 4 H), 2.70 (brs, 4 H), 1.33 (d, J=5.97 Hz, 6 H); MS (ES) m/z: 489 (MH+).

Example 18

Cpd. 18

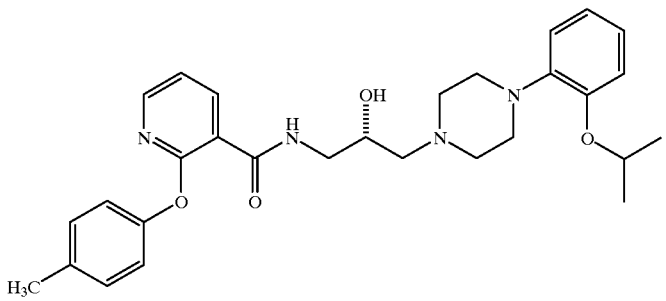

Piperazine 7 (150 mg, 0.51 mmol) was dissolved in a mixture of diisopropylethylamine (0.35 mL) and methylene chloride (2 mL). 2-(4-Methylphenoxy)pyridine-3-carbonyl chloride (126 mg, 0.51 mmol) and DMAP (cat.) were added into the above methylene chloride solution. The mixture was stirred at 20° C. for 16 h and concentrated. The product was purified by column chromatography (silica gel) to yield compound 18 (146 mg, 57%) as a foam: MS (ES) m/z: 505 (MH+).

Example 19

Cpd. 19

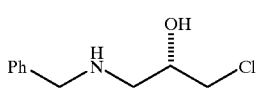

A mixture of (S)-(+)-epichlorohydrin (10 g, 108.1 mmol, Aldrich, 97% ee) and benzylamine (11.57 g, 108.1 mmol) in hexane (40 mL) were stirred at 20° C. for 62 h. White solid precipitated. More hexane (~350 mL) added, stirred for 20 min. and sonicated to break the big chunks of white solid. The white solid was collected by filtration and washed with hexane, dried under vacuum to give 19.8 g (92%) white solid. The white solid was recrystallized from EtOAc/hexane to give 17.76 g (82%) of 1 as a white crystallined solid; $^1$H NMR (300 MHz, CDCl$_3$) δ 7.31 (m, 5 H), 3.88 (m, 1 H), 3.79 (m, 2 H), 3.53 (d, J=5.3 Hz, 2 H), 2.89 (m, 2 H), 2.81 (dd, J=12.4, 4.1 Hz, 1 H), 2.69 (dd, J=12.2, 7.9 Hz, 1 H); MS (ES): 200 (MH+); Anal. Calcd. for C$_{10}$H$_{14}$NOCl: C, 60.15; H, 7.07; N, 7.01. Found: C, 60.10; H, 7.02; N, 6.92.

Example 20

Cpd. 20

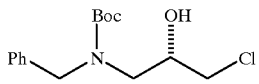

Boc$_2$O (11 g, 50.1 mmol) and triethylamine (10.12 g, 100 mmol) were dissolved in THF (25 mL) and cooled to 0° C. The amine 19 (10 g, 50.1 mmol) was added in portions and stirred for 20 h while the temperature was warm up to 20° C. overnight. The solvent was concentrated in vacuo and water added. The mixture was extracted with ether (3x), dried (Na$_2$SO$_4$) and concentrated. The crude residue was recrystallized from EtOAc/hexane to give 9.9 g (66%) of 20 as a white crystallined solid. The filtrate was concentrated (3.1 g as oil) and more product was purified by column chromatography (short column, 8 cm height of SiO$_2$, EtOAc/hexane as solvent). The oil was recrystallized from EtOAc/hexane to give another 2.78 g (18%) of 20 as a white crystalline solid; [α]$_D^{25}$=−10.20 (c=1, CHCl$_3$); $^1$H NMR (300 MHz, CDCl$_3$) δ 7.22–7.36 (m, 5 H), 4.52 (m, 2 H), 4.30 (brs, 0.5 H), 3.96 (m, 1 H), 3.36–3.97 (m, 4 H), 1.47 (s, 9 H); MS (ES): 322 (M+Na); Anal. Calcd. for C$_{15}$H$_{22}$NO$_3$Cl: C, 60.10; H, 7.40; N, 4.67. Found: C, 60.26, H, 7.42; N, 4.63

Example 21

Cpd. 21

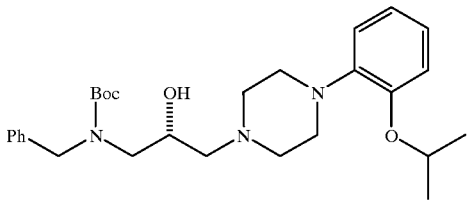

KOH (11.23 g, 200.5 mmol) was dissolved in methanol (280 mL), and the fumarate salt of 1-(2-isopropoxyphenyl)-piperazine (10.9 g, 33.4 mmol) was added and stirred at 20° C. for 20 min then cooled to 0° C. The Boc-protected amine 20 (10 g, 33.4 mmol) was added to the methanol solution at 0° C. and stirred for 20 h while the temperature was warm up to 20° C. overnight. The solvent was removed, water was added and the mixture was extracted with ether (3x), dried (Na$_2$SO$_4$) and concentrated. The product was purified by column chromatography (short column, 8 cm height SiO$_2$, EtOAc/hexane as solvent) to give 10.22 g (63%) of 3 (~100% ee, Chiralpak OD 4.6x250 mm. 1 mL/min, 254 nm, mobile phase: 90/10/0.1 of hexane/IPA/0.1% diethylamine) as a yellowish oil; $^1$H NMR (300 MHz, CDCl$_3$) δ 7.26–7.35 (m, 5 H), 6.91 (m, 4 H), 4.68 (d, J=15.6 Hz, 1 H), 4.59 (m, 3 H), 3.95 (m, 1 H), 3.35 (m, 2 H), 3.11 (m, 4 H), 2.75 (m, 2 H), 2.54 (m, 2 H), 2.38 (m, 2 H), 1.45 (m, 9 H), 1.34 (d, J=6.1 Hz, 6 H); MS (ES): 484 (MH+).

Example 22

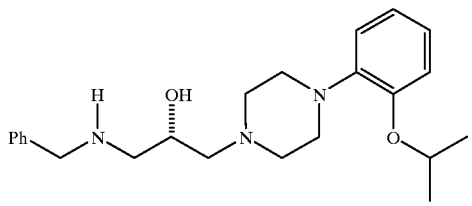

Cpd. 22

A mixture of compound 21 (233 mg, 0.48 mmol) and 25% TFA/methylene chloride (3 mL) was stirred at 20° C. for 18 h. The solvent was concentrated in vacuo and the residue was basified with 20% NaOH (aq), extracted with methylene chloride (3x), dried ($Na_2SO_4$) and concentrated to give 174 mg (~95%) of 22 as an oil. Used directly without further purification; MS (ES): 384 ($MH^+$).

Example 23

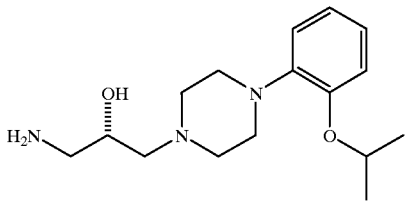

Cpd. 23

To a mixture of 22 (~154 mg, 0.4 mmol) and 10% Pd/C (154 mg) in EtOH (3 mL) was added ammonium formate (151 mg, 2.4 mmol) and stirred at 55–60° C. for 20 h. The mixture was filtered thru celite and washed with methanol. The filtrate was concentrated. The product was purified by a short column (5 cm height of $SiO_2$) to give 63 mg (54%) of 23 as a oil; $[\alpha]_D^{25}$ +23.60° (c=1, CHCl3); 1H NMR (300 MHz, CDCl3) δ 6.91 (m, 4 H), 4.59 (m, 1 H), 3.76 (m, 1 H), 3.12 (m, 4 H), 2.83 (dd, J=12.7, 3.7 Hz, 2 H), 2.82 (m, 1 H), 2.25–2.68 (m, 8 H), 1.34 (d, J=6.1 Hz, 6 H); MS (ES): 294 ($MH^+$).

BIOLOGICAL EXAMPLES

The biological activity and selectivity of compounds of the invention was demonstrated by the following assays. The first assay tested the ability of compounds of Formula I to bind to membrane bound receptors $\alpha 1_a$-AR, $\alpha 1_b$-AR and $\alpha 1_d$-AR.

Example 24

The DNA sequences of the three cloned human α1-AR subtypes have been published. Furthermore, the cloned cDNAs have been expressed both transiently in COS cells and stably in a variety of mammalian cell lines (HeLa, LM(tk−), CHO, rat-1 fibroblast) and have been shown to retain radioligand binding activity and the ability to couple to phosphoinositide hydrolysis. We used published DNA sequence information to design primers for use in RT-PCR amplification of each subtype to obtain cloned cDNAs. Human poly A+ RNA was obtained from commercially available sources and included hippocampus and prostate samples, sources which have been cited in the literature. For the primary screen a radio ligand binding assay was used which employed membrane preparations from cells expressing the individual cloned receptor cDNAs. Radiolabeled ligands with binding activity on all three subtypes (non-selective) are commercially available ([125I]-HEAT, [3H]-prazosin).

Each α1 receptor subtype was cloned from poly A+ RNA by the standard method of reverse transcription-polymerase chain reaction (RT-PCR). The following sources of polyA+ RNA were used for the cloning of the α1 receptor subtypes: $\alpha 1_a$-AR, human hippocampus and prostate, $\alpha 1_b$-AR, human hippocampus, $\alpha 1_d$-AR, human hippocampus. The resulting cDNAs were cloned into the pcDNA3 mammalian expression vector (Invitrogen Corp., San Diego Calif.). Each DNA was sequenced for verification and to detect any possible mutations introduced during the amplification process. Any deviation in sequence from the published consensus for each receptor subtype was corrected by site-directed mutagenesis.

The three α1-AR subtypes (a, b, d) were transfected into COS cells using a standard DEAE-dextran procedure with a chloroquine shock. In this procedure, each tissue culture dish (100 mm) was inoculated with $3.5 \times 10^6$ cells and transfected with 10 μg of DNA. Approximately 72 hours post-transfection, the cells were harvested and COS membranes were prepared. Transfected COS cells from 25 plates (100 mm) were scraped and suspended in 15 mL of TE buffer (50 mM Tris-HCl, 5 mM EDTA, pH7.4). The suspension was disrupted with a homogenizer. It was then centrifuged at 1000×g for 10 minutes at 40° C. The supernatant was centrifuged at 34,500×g for 20 minutes at 4° C. The pellet was resuspended in 5 mL TNE buffer (50 mM Tris-HCl, 5 mM EDTA, 150 mM NaCl, pH7.4). The resulting membrane preparation was aliquoted and stored at −70° C. The protein concentration was determined following membrane solubilization with TritonX-100.

The ability of each compound to bind to each of the α1-AR subtypes was assessed in a receptor binding assay. [125I]-HEAT, a non-selective α1-AR ligand, was used as the radiolabeled ligand. Each well of a 96-well plate received: 140 μL TNE, 25 μL [125I]-HEAT diluted in TNE (50,000 cpm; final concentration 50 pM), 10 μL test compound diluted in DMSO (final concentration 1 pM-10 μM), 25 mL COS cell membrane preparation expressing one of the three α1-AR subtypes (0.05–0.2 mg membrane protein). The plate was incubated for 1 hour at room temperature and the reaction mixtures were filtered through a Packard GF/C Unifilter filter plate. The filter plate was dried for 1 hour in a vacuum oven. Scintillation fluid (25 mL) was added to each well, and the filter plate was counted in a Packard Topcount scintillation counter. Data was analyzed using GraphPad Prism software.

Tables A lists $IC_{50}$ values expressed in nanomolar concentration for select compounds of the invention in all receptor subtypes.

TABLE A

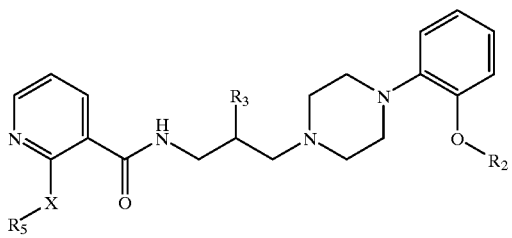

| Cpd. | X | R₂ | R₃ | R₅ | α1a | α1b | α1d |
|---|---|---|---|---|---|---|---|
| 3 | O | i-propyl | OH | Ph | 1.5 | 909 | 211 |
| 5 | O | i-propyl | H | Ph | 0.64 | 151 | 40 |
| 8 | O | i-propyl* | OH | Ph | 0.76 | 668 | 81 |
| 35 | O | i-propyl** | OH | Ph | 10.2 | 889 | 314 |
| 10 | O | i-propyl | OH | 4-OCH₃—Ph | 2.4 | 1910 | 131 |
| 36 | O | i-propyl | OH | 4-F—Ph | 1.5 | 1182 | 148 |
| 37 | O | i-propyl | OH | 3-Cl—Ph | 0.91 | 952 | 180 |
| 38 | O | i-propyl | OH | 3-N(CH₃)₂—Ph | 2 | 972 | 56 |
| 39 | O | i-propyl | OH | 2-CH₃—Ph | 1.1 | 730 | 1.7 |
| 40 | O | i-propyl | OH | 2-OCH₃—Ph | 1.7 | 580 | 2.2 |
| 11 | NH | i-propyl | OH | 3-CF₃—Ph | 25 | 1020 | 79 |
| 12 | S | i-propyl | OH | 4-Cl—Ph | 2.6 | 806 | 299 |
| 41 | O | i-propyl | OH | 4-CH₃—Ph | 0.52 | 928 | 21 |
| 42 | O | i-propyl | OH | 4-Cl—Ph | 1 | 838 | 74 |
| 43 | S | i-propyl | OH | Ph | 2 | 1220 | 70 |
| 18 | O | i-propyl* | OH | 4-CH₃—Ph | 0.51 | 290 | 50 |
| 27 | O | i-propyl* | OH | 4-Cl—Ph | 0.86 | 791 | 57 |
| 28 | O | i-propyl** | OH | 4-CH₃—Ph | 25 | 361 | 969 |
| 29 | O | i-propyl | H | 4-CH₃—Ph | 0.27 | >2000 | 43 |
| 30 | O | i-propyl | OH | 3,4-di-Cl—Ph | 2 | 2251 | 56 |
| 31 | NH | i-propyl | OH | Ph | 25 | 736 | 25 |
| 32 | O | CH₃ | OH | Ph | 30 | 1570 | 147 |
| 13 | O | i-propyl | OH | CH₃ | 3.5 | >2,000 | 191 |
| 33 | O | i-propyl | OH | 4-(CH₃)₃C—Ph | 3.3 | >2,000 | 78 |
| 34 | O | CH₃CH₂ | OH | Ph | 9.1 | 132 | 206 |
| 16 | O | i-propyl | OCH₃ | Ph | 2.4 | 1356 | 21 |
| 17 | O | i-propyl | O | 4-(CH₃)₃C—Ph | 63 | 887 | 546 |

*indicates "S" stereochemistry
**indicates "R" stereochemistry

Example 25

The antagonist activity and the selectivity of compounds of the invention for prostate tissues over aortic tissues as well as their antagonists was demonstrated as follows. The contractile responses of rat prostatic tissue and rat aorta tissues were examined in the presence and absence of antagonist compounds. As an indication of the selectivity of antagonism, test compound effects on vascular smooth muscle contractility ($\alpha1_b$-AR and $\alpha1_d$-AR) were compared to the effects on prostatic smooth muscle ($\alpha1_a$-AR). Strips of prostatic tissue and aortic rings were obtained from Long Evans derived male rats weighing 275 grams and sacrificed by cervical dislocation. The prostate tissue was placed under 1 gram tension in a 10 ml bath containing phosphate buffered saline pH 7.4 at 32° C. and isometric tension was measured with force transducers. The aortic tissue was placed under 2 grams tension in a 10 ml bath containing phosphate buffered saline pH 7.4 at 37° C. The ability of test compound to reduce the norepinephrine-induced contractile response by 50% ($IC_{50}$) was determined. Compound 3 inhibited the contractile response in aortic tissue with an $IC_{50}$ of 4.74 $\mu$M and in prostate tissue with an $IC_{50}$ of 0.143 $\mu$M. Compound 35 inhibited the contractile response in aortic tissue with an $IC_{50}$ of 8.5 $\mu$M and in prostate tissue with an $IC_{50}$ of 0.18 $\mu$M.

Example 26

Select compounds of the invention were tested for their ability to antagonize phenylephrine (PE) induced increases in intraurethral pressure in dogs. The selectivity of these compounds was demonstrated by comparing their effect upon PE induced increases in mean arterial pressure (MAP) in the dog.

Male beagle dogs were anesthetized and catheterized to measure intraurethral pressure (IUP) in the prostatic urethra. Mean arterial pressure (MAP) was measured using a catheter placed in the femoral artery. Dogs were initially administered six i.v. bolus doses (1 to ≦32 mg/kg) of phenylephrine (PE) to establish a control agonist dose-response curve. IUP and MAP were recorded following each dose until the IUP returned to baseline. The dogs then were given an i.v. bolus dose of the antagonist compound, followed by i.v. PE challenges of ascending doses, as in the control agonist dose-response curve. IUP and MAP measurements following each PE challenge were recorded. The antagonist compound was tested over a dose range of 3 to 300 ug/kg in half-log increments. The interval between antagonist doses was at least 45 min and three experiments were performed for each test compound. FIG. 1 illustrates the mean percentage reductions in IUP and MAP for Compound 8. (See FIG. 1)

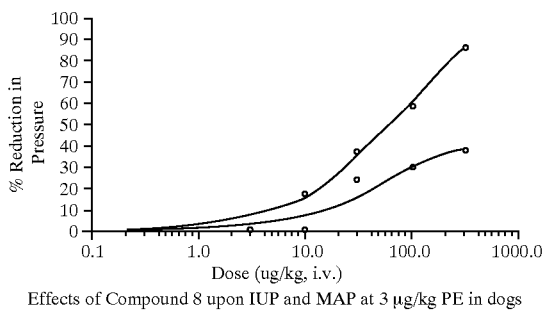

Effects of Compound 8 upon IUP and MAP at 3 μg/kg PE in dogs
- ■ IUP
- ● MAP

REFERENCES

M. Barry & C. Roehborn, Management of Benign Prostatic Hyperplasia, 48 Annu. Rev. Med. 177–89 (1997), Bruno J F, Whittaker J, Song J, and Berelowitz M. (1991) Molecular cloning and sequencing of a cDNA encoding a human α1A adrenergic receptor. Biochem. Biophys. Res. Commun. 179: 1485–1490.

Forray C, Bard J A, Wetzel J M, Chiu G, Shapiro E, Tang R, Lepor H, Hartig P R, Weinshank R L, Branchek T A, and Gluchowski C (I1994). The α1-adrenergic receptor that mediates smooth muscle contraction in human prostate has the pharmacological properties of the cloned human α1c subtype. Mol. Pharmacol. 45: 703–708.

Gormley G, Stoner E, Bruskewitz R C et al. (1992) The effect of finasteride in men with benign prostatic hyperplasia. N. Engl. J. Med. 327: 1185–1191.

Hatano A, Takahashi H, Tamaki M, Komeyama T, Koizumi T, and Takeda M (1994) Pharmacological evidence of distinct α1-adrenoceptor subtypes mediating the contraction of human prostatic urethra and peripheral artery. Br. J. Pharmacol. 113: 723–728.

Harrison J K, Pearson W R, and Lynch K R (1991) Molecular characterization of α1- and α2-adrenoceptors. Trends Pharmacol. Sci. 12: 62–67.

Hieble J P and Caine M (1986) Etiology of benign prostatic hyperplasia and approaches to pharmacological management. Fed. Proc. 45: 2601–2603.

Hirasawa A, Horie K, Tanaka T, Takagaki K, Murai M, Yano J, and Tsujimoto G (1993) Cloning, functional expression and tissue distribution of human cDNA for the α1c-adrenergic receptor. Biochem. Biophys. Res. Commun. 195: 902–909.

Lepor H and Rigaud G (1990) The efficacy of transurethral resection of the prostate in men with moderate symptoms of prostatism. J. Urol. 143: 533–537.

Lepor H, Auerbach S, Puras-Baez A et al. (1992) A randomized, placebo-controlled multicenter study of the efficacy and safety of terazosin in the treatment of benign prostatic hyperplasia. J. Urol. 148: 1467–1474.

Lepor H (1995) α-Blockade for benign prostatic hyperplasia (BPH) J. Clin. Endocrinol. Metab. 80: 750–753.

Marshall I, Burt R P, Andersson P O, Chapple C R, Greengrass P M, Johnson G I, and Wyllie M G (1992) Human α1c-adrenoceptor: functional characterisation in prostate. Br. J. Pharmacol. 107(Proc. Suppl. Dec.):327P.

Marshall I, Burt R P, and Chapple C R (1995) Noradrenaline contractions of human prostate mediated by α1A-(α1c-)adrenoceptor subtype. Br. J. Pharmacol. 115: 781–786.

Mebust W K, Holtgrewe H L, Cockett A T K, and Peters P C (1989) Transurethral prostatectomy: immediate and postoperative complications. A cooperative study of 13 participating institutions evaluating 3,885 patients.J. Urol., 141: 243–247.

Oesterling J E (1995) Benign prostatic hyperplasia. Medical and minimally invasive treatment options. N. Engl. J. Med. 332: 99–109.

Ramarao C S, Kincade Denker J M, Perez D M, Gaivin R J, Riek R P, and Graham R M (1992) Genomic organization and expression of the human α1B-adrenergic receptor. J. Biol. Chem. 267: 21936–21945.

Schwinn D A, Johnston G I, Page S O, Mosley M J, Wilson K H, Worman N P, Campbell S, Fidock M D, Furness L M, Parry-Smith D J, Peter B, and Bailey D S (1995) Cloning and pharmacological characterization of human alpha-1 adrenergic receptors: sequence corrections and direct comparison with other species homologues. JPET 272: 134–142.

William D. Steers & Burkhart Zorn, *Benign Prostatic Hyperplasia*, in Disease-a-Month (M. Greenbeerger et al. Eds., 1995).

Weinberg D H, Trivedi P, Tan C P, Mitra S, Perkins-Barrow A, Borkowski D, Strader C D, and Bayne M (1994) Cloning, expression and characterization of human α adrenergic receptors α1A, α1B, and α1C. Biochem. Biophys. Res. Commun. 201: 1296–1304.

Weis K A, Epstein R S, Huse D M, Deverka P A and Oster G (1993). The costs of prostatectomy for benign prostatic hyperplasia. Prostate 22: 325–334.

Wennberg J E, Roos N, Sola L, Schori A, and Jaffe R (1987). Use of claims data systems to evaluate health care outcomes: mortality and reoperation following prostatectomy. JAMA 257: 933–936.

Yamada S, Tanaka C, Kimura R, and Kawabe K (1994) Alpha 1-adrenoceptors in human prostate: characterization and binding characteristics of alpha 1-antagonists. Life Sci. 54: 1845–1854.

What is claimed is:

1. A compound of Formula I

![Formula I structure]

$R_1$ is hydrogen, halogen, $C_{1-5}$alkoxy, hydroxyl, or $C_{1-5}$alkyl;

$R_2$ is $C_{1-6}$alkyl, substituted $C_{1-6}$alkyl
  where the alkyl substituents are independently selected from one or more halogens,
  phenyl, substituted phenyl
  where the phenyl substituents are independently selected from one or more members of the group consisting of $C_{1-5}$alkyl, $C_{1-5}$alkoxy, and trihalo$C_{1-5}$alkyl,
  phenyl$C_{1-5}$alkyl, or substituted phenyl$C_{1-5}$alkyl
  where the phenyl substituents are independently selected from one or more members of the group consisting of $C_{1-5}$alkyl, halogen, $C_{1-5}$alkoxy, and trihalo$C_{1-5}$alkyl;

$R_3$ is hydrogen, hydroxy or $C_{1-5}$alkoxy if the dashed line is absent or is oxygen if the dashed line is present;

$R_4$ is hydrogen, $C_{1-5}$alkyl, phenyl$C_{1-5}$alkyl or substituted phenyl$C_{1-5}$alkyl
  where the phenyl substituents are independently selected from one or more members of the group consisting of $C_{1-5}$alkyl, $C_{1-5}$alkoxy, and trihalo$C_{1-5}$alkyl;

$R_5$ is $C_{1-6}$alkyl,
  substituted $C_{1-6}$alkyl
    where the alkyl substituents are independently selected from one or more halogens,
  phenyl, substituted phenyl
    where the phenyl substituents are independently selected from one or more members of the group consisting of $C_{1-8}$alkyl, hydrogen, halogen, hydroxy, $C_{1-8}$alkyl, substituted $C_{1-8}$alkyl
      where the alkyl substituents are independently selected from one or more halogens,
    $C_{1-5}$alkoxy, amino, $C_{1-5}$alkylamino, di$C_{1-5}$alkylamino, $C_{1-5}$alkylcarbonyl, $C_{1-5}$alkoxycarbonyl, arylcarbonyl, nitrile, aminosulfonyl, $C_{1-5}$alkylsulfonyl, phenylsulfonyl, and substituted phenylsulfonyl
      where the phenyl substituents are independently selected from one or more members the group consisting of $C_{1-8}$alkyl hydrogen, halogen, hydroxy and nitro;
  phenyl$C_{1-5}$alkyl, substituted phenyl$C_{1-5}$alkyl
    where the phenyl substituents are independently selected from one or more members of the group consisting of $C_{1-8}$alkyl hydrogen, halogen, hydroxy, $C_{1-8}$alkyl, substituted $C_{1-8}$alkyl
      where the alkyl substituents are independently selected from one or more halogens, $C_{1-5}$alkoxy, amino, $C_{1-5}$alkylamino, di$C_{1-5}$alkylamino, $C_{1-5}$alkylcarbonyl, $C_{1-5}$alkoxycarbonyl, and nitro;

X is oxygen, sulfur or NH;
pharmaceutically acceptable salts thereof;
and stereoisomers, racemic mixtures, as well as enantiomers thereof.

2. The compound of claim 1 wherein $R_3$ is oxygen.

3. The compound of claim 1 wherein $R_3$ is hydrogen or hydroxy.

4. The compound of claim 3 wherein $R_1$ is hydrogen, halogen, or hydroxy, $R_2$ phenyl, hydrogen or $C_{1-6}$alkyl, $R_4$ is $C_{1-5}$alkyl or hydrogen, and $R_5$ is $C_{1-5}$alkyl, phenyl or substituted phenyl and X is sulfur or oxygen.

5. The compound of claim 4 wherein $R_1$ is hydrogen, $R_2$ is $C_{1-5}$alkyl, $R_3$ is hydroxy, $R_4$ is hydrogen, $R_5$ is substituted phenyl and X is oxygen.

6. The compound of claim 1 wherein $R_1$ is hydrogen, $R_2$ is i-propyl, $R_3$ is hydroxy or hydrogen, $R_4$ is hydrogen, $R_5$ is phenyl or substituted phenyl where the phenyl substitutents are independently selected from one or more members of the group consisting of $C_{1-5}$alkoxy, halogen, di$C_{1-5}$alkylamino $C_{1-5}$alkyl, and halogen substituted $C_{1-5}$alkyl, and X is oxygen.

7. The compound of claim 1 where $R_1$ is hydrogen, $R_2$ is i-propyl, $R_3$ is hydroxy, $R_4$ is hydrogen, $R_5$ is phenyl, X is oxygen and the stereochemistry of the chiral carbon is S.

8. A method of treating benign prostatic hyperplasia consisting of administering an effective dose of a compound of claim 1 to a mammal.

9. The method of claim 8 where the effective dose is about 0.1 to about 25.0 mg/kg.

10. A pharmaceutical composition comprising an effective dose of a compound of claim 1 and a pharmaceutically acceptable carrier.

11. A pharmaceutical composition of claim 10 where the effective dose of a compound of Formula I is about 0.1 to about 25.0 mg/kg.

12. A pharmaceutical composition of claim 10 where the effective dose of a compound of Formula I is about 0.01 to about 1.0 mg/kg.

* * * * *